United States Patent
Gerber et al.

(10) Patent No.: US 8,260,436 B2
(45) Date of Patent: Sep. 4, 2012

(54) IMPLANTABLE STIMULATION LEAD WITH FIXATION MECHANISM

(75) Inventors: Martin T. Gerber, Maple Grove, MN (US); John M. Swoyer, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 954 days.

(21) Appl. No.: 10/698,291

(22) Filed: Oct. 31, 2003

(65) Prior Publication Data

US 2005/0096718 A1     May 5, 2005

(51) Int. Cl.
*A61N 1/00* (2006.01)
(52) U.S. Cl. .......................................... 607/117
(58) Field of Classification Search .............. 607/117, 607/119; 606/41; 623/1.18, 1.19
See application file for complete search history.

(56) References Cited

U.S. PATENT DOCUMENTS

| | | | |
|---|---|---|---|
| 5,531,779 A * | 7/1996 | Dahl et al. .................. 607/119 |
| 5,733,322 A * | 3/1998 | Starkebaum ................ 607/117 |
| 6,077,298 A * | 6/2000 | Tu et al. ...................... 623/1.19 |
| 6,146,380 A * | 11/2000 | Racz et al. .................. 606/41 |
| 6,192,279 B1 * | 2/2001 | Barreras et al. ............ 607/117 |
| 6,360,750 B1 | 3/2002 | Gerber et al. |
| 6,510,347 B2 | 1/2003 | Borkan |
| 6,567,704 B2 * | 5/2003 | Sundquist et al. ........... 607/119 |
| 7,255,695 B2 * | 8/2007 | Falwell et al. .............. 606/41 |
| 2002/0161423 A1 | 10/2002 | Lokhoff et al. |
| 2003/0045919 A1 | 3/2003 | Swoyer et al. |
| 2008/0103573 A1 | 5/2008 | Gerber et al. |

OTHER PUBLICATIONS

"Bagley Helical Baskets," http://www.bsci.com/prod_db_mvu/se...on=displayUnique&product_row_id=51, 1 pg.
"Pursuer™ Helical Baskets," http://www.bsci.com/prod_db_mvu/se...ion=showDiagrams&product_row_id=52, 1 pg.
"Gemini™ Paried Wire Helical Baskets," http://www.bsci.com/prod_db_mvu/se...ion=showDiagrams&product_row_id=50, 2 pgs.
Office Action dated Jun. 25, 2009 for U.S. Appl. No. 11/591,282 (8 pgs.).
Responsive Amendment dated Sep. 24, 2009 for U.S. Appl. No. 11/591,282 (12 pgs.).
Office Action dated Dec. 28, 2009 for U.S. Appl. No. 11/591,282, (8 pgs.).
Request for Continued Examination and Responsive Amendment dated Mar. 25, 2010 for U.S. Appl. No. 11/591,282, (15 pgs.).
Office Action dated Oct. 7, 2011 for U.S. Appl. No. 11/591,282, (9 pgs.).

* cited by examiner

*Primary Examiner* — George Manuel
(74) *Attorney, Agent, or Firm* — Shumaker & Sieffert, P.A.

(57) ABSTRACT

An implantable electrical stimulation lead includes an integrated fixation mechanism that expands upon implantation of the lead to fix the lead relative to a target tissue site, such as tissue within the epidural region proximate the spine or the sacral foramen. The fixation mechanism may include one or more expandable wire-like elements, which may be configured in a substantial helical shape. The wire-like elements may be formed from an elastic or super-elastic material, and expand radially outward when a restraint mechanism is removed following implantation of the lead.

65 Claims, 7 Drawing Sheets

IMPLANTABLE STIMULATION LEAD WITH FIXATION MECHANISM

TECHNICAL FIELD

The invention relates to neurostimulation systems, and more specifically, to stimulation leads in neurostimulation systems.

BACKGROUND

Neurostimulation systems may be used to deliver neurostimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, incontinence, or gastroparesis. A neurostimulation system delivers neurostimulation therapy in the form of electrical pulses. In general, neurostimulation systems deliver neurostimulation therapy via electrodes on stimulation leads located proximate to the spinal cord, pelvic nerves, pudendal nerve, or stomach, or within the brain of a patient. The stimulation leads may include percutaneously implanted leads or surgically implanted leads.

Neurostimulation techniques may involve stimulation leads for stimulating nerves located in the epidural region, the sacral region, and the like. Stimulation of the sacral region can provide therapy for a variety of pelvic floor disorders such as urinary control disorders, fecal control disorders, interstitial cystitis, sexual dysfunction, and pelvic pain. In particular, the organs involved in various bodily functions receive much of their control via the second, third, and fourth sacral nerves, commonly referred to as S2, S3, and S4, respectively. The sacrum, in general, is a large, triangular bone situated at the lower part of the vertebral column, and at the upper and back part of the pelvic cavity. The spinal canal runs throughout the sacrum. The sacral nerves pass through the sacrum via the anterior and posterior sacral foramina. These organs are also innervated via other nerves, such as the pudendal nerve.

Electrical stimulation of the sacral nerves, pudendal nerves, and other nerves of the pelvic floor has been found to offer relief for many pelvic floor disorders. For example, medical leads having discrete electrodes are implanted on and near the sacral nerves. An implantable pulse generator drives the electrodes with an electrical signal to stimulate the sacral nerves, and thereby restore or control bodily functions affected by pelvic floor disorders. Several techniques of electrical stimulation may be used, including stimulation of nerve bundles within the sacrum.

Successful electrical stimulation generally requires that a neurostimulation lead does not migrate from a target site following implantation. Securing a neurostimulation lead at the target site may minimize lead migration. One method for securing a neurostimulation lead in a desired location includes suturing the lead to surrounding tissue. However, suturing a neurostimulation lead may involve an invasive surgery. Another method of reducing lead migration includes the use of a tined lead, which includes a lead body with protruding tines that fixate the neurostimulation lead within tissue surrounding the lead.

U.S. patent Publication No. 20030045919 to Swoyer et al. describes an implantable medical electrical lead for stimulation of the sacral nerves. The lead described by Swoyer et al. comprises a lead body with an array of flexible tine elements to fixate the lead within a. tissue site. U.S. patent Publication No. 20020161423 to Lokhoff et al. describes a transvenous lead with an extendable distal fixation member such as a helix. The fixation member described by Lokhoff et al. may be a helix, constructed of a shape memory metal or other super-elastic material, that functions to wedge or fix the lead within a vessel. U.S. Pat. No. 6,360,750 to Gerber et al. describes implantation of leads for neurostimulation within the sacral region. Table 1 below lists documents that disclose lead systems with fixation mechanisms.

TABLE 1

| Patent Number | Inventors | Title |
| --- | --- | --- |
| 20030045919 | Swoyer et al. | Implantable medical electrical stimulation lead fixation method and apparatus |
| 20020161423 | Lokhoff et al. | System and method for positioning an implantable medical device within a body |
| 6,360,750 | Gerber et al. | Minimally invasive surgical techniques for implanting devices that deliver stimulant to the nervous system |

All documents listed in Table 1 above are hereby incorporated by reference herein in their respective entireties. As those of ordinary skill in the art will appreciate readily upon reading the Summary, Detailed Description and Claims set forth below, many of the devices and methods disclosed in the patents of Table 1 may be modified advantageously by using the techniques of the present invention.

SUMMARY

The present invention is directed to an implantable neurostimulation device and leads useful with an implantable neurostimulation device, as well as methods for implantation of leads. The invention has certain objects. That is, various embodiments of the present invention provide solutions to one or more problems existing in the prior art with respect to implantable stimulation leads.

Such problems include, for example, difficulty in providing effective fixation of implantable stimulation leads without invasive surgical procedures, e.g., using sutures. Surgical procedures can cause patient pain and discomfort, and requires additional recovery time following lead implantation. Additional problems, in the absence of effective fixation, include potential migration of stimulation leads with the possibility of adverse impacts on stimulation efficacy. Other problems relate to difficulty in deploying a fixation mechanism, such as tines, and further difficulty in explanting stimulation leads secured with such a fixation mechanism.

Various embodiments of the present invention have the object of solving at least one of the foregoing problems. For example, it is an object of the present invention to provide a mechanism for effective fixation of an implantable stimulation lead. It is a further object to provide a fixation mechanism that reduce patient pain and discomfort during implantation. Another object is to provide a fixation mechanism that avoids lead migration. Other objects are to provide a lead with a fixation mechanism that is less difficult to deploy, and presents less difficulty upon lead explant, if necessary.

Various embodiments of the invention may possess one or more features capable of fulfilling the above objects. In general, the invention relates to a minimally invasive technique for reducing migration by fixating a neurostimulation lead to a target therapy site within a patient. In particular, a fixation mechanism may be mounted to a neurostimulation lead to fixate the lead to any tissue surrounding the lead, such as tissue within the epidural region or, in some applications, proximate to a sacral foramen. The fixation mechanism may include one or more of expandable wire-like elements, which may be configured in a substantial helical shape in some embodiments. The wire-like elements may expand radially outward from a stimulation lead body. The material of the wire-like elements may have elastic or super-elastic properties that cause the wire-like elements to expand against surrounding tissue, and thereby fix the lead at a desired location.

The expandable fixation mechanism may be restrained from expansion by a restraint mechanism. A restraint mechanism may include a lead introducer, which comprises a lead introducer lumen sized to accommodate a stimulation lead body and the restrained fixation mechanism. Alternatively, a restraint mechanism may include a stylet that is accommodated by an inner lumen of the neurostimulator. The stylet may straighten, extend, or stretch a portion of the neurostimulator lead body, thereby restraining wire-like elements of the fixation mechanism from expansion. Upon release of the restraint mechanism, the fixation mechanism expands radially outward to engage the surrounding tissue. The lead body and restrained fixation mechanism may be sized for minimally invasive implantation techniques, and does not require surgical implantation. In some embodiments, the restraint mechanism may have a collapsible or breakable structure that facilitates explant of stimulation leads.

A neurostimulation lead, in accordance with the invention, comprises a lead body having a proximal end and a distal end. A plurality of stimulation electrodes are disposed adjacent the distal end of the lead body. A fixation mechanism is mounted to the lead body at a position between one of the electrodes and the proximal end of the lead body, and includes a plurality of wire-like elements that are expandable to fix the lead body at a tissue target site.

A method for implanting a lead, in accordance with the invention, comprises inserting a lead introducer into a patient, and inserting a lead into the patient via the introducer. The lead includes a lead body having a proximal end and a distal end, a plurality of stimulation electrodes disposed adjacent the distal end of the lead body. A fixation mechanism is mounted to the lead body at a position between one of the electrodes and the proximal end of the lead body, and includes a plurality of wire-like elements that are expandable to fix the lead body at a tissue target site. The method may further include removing a restraint mechanism on the fixation mechanism, thereby permitting the wire-like elements to expand. In some embodiments, restraint may be provided by the introducer, a stylet, or other mechanisms.

In comparison to known implementations of neurostimulators, various embodiments of the present invention may provide one or more of advantages. In particular, the invention provides a technique for effective fixation of an implanted stimulation lead to prevent lead migration. By preventing migration, the fixation mechanism maintains the position of the lead electrodes to ensure delivery of stimulation energy to a desired site. The technique, which may include introducing the lead body and fixation mechanism via a needle, requires only minimally invasive implantation techniques, thereby reducing patient pain, discomfort and recovery time, and may not require the efforts of a surgeon. In addition, the fixation mechanism may facilitate explant of the stimulation lead.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
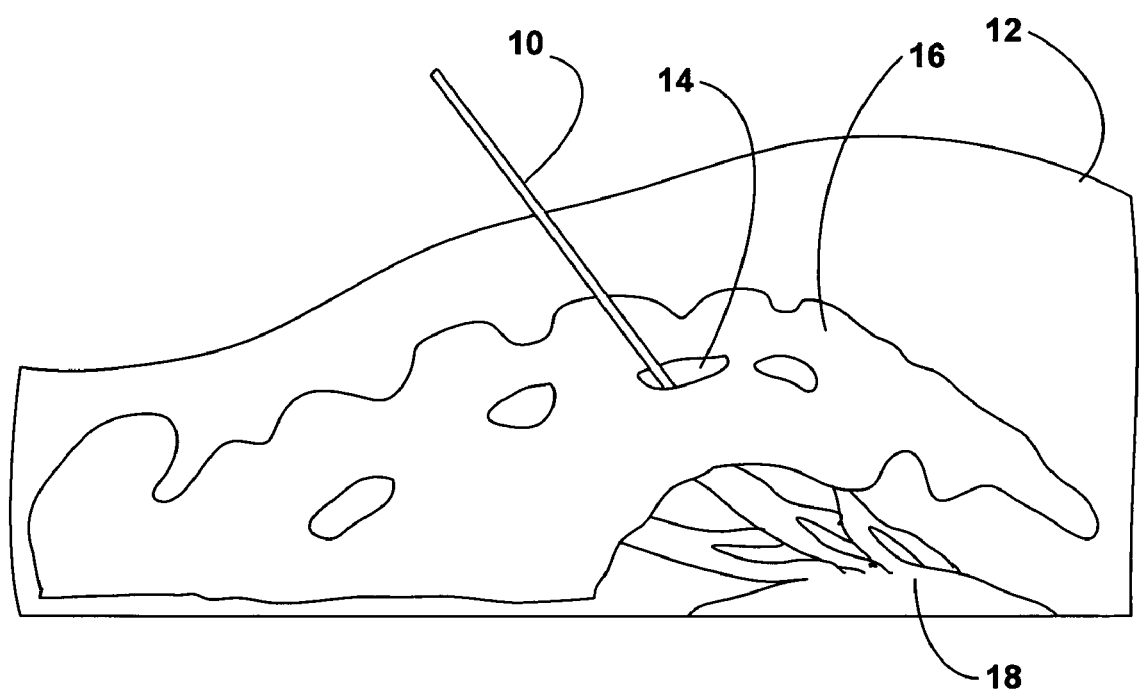
FIG. 1 is a diagram illustrating sacral implantation of a neurostimulation lead.

FIG. 1 is a diagram illustrating implantation of a neurostimulation lead 10. In the example of FIG. 1, lead 10 is inserted into body 12 of a patient, and implanted posterior to one of dorsal foramen 14 of sacrum 16. However, lead 10 alternatively may be positioned to stimulate pudendal nerves, perineal nerves, or other areas of the nervous system. As further alternatives, lead 10 may be positioned for temporary or chronic spinal cord stimulation for the treatment of pain, or for gastric stimulation for the treatment of gastric mobility disorders and obesity, or for deep brain stimulation to treat movement disorders and other neurological disorders. Accordingly, although sacral nerve stimulation will be described herein for purposes of illustration, a neurostimulation lead 10 in accordance with the invention may be adapted for application to a variety of electrical stimulation applications.

Lead 10 may be implanted via a needle and stylet for minimal invasiveness. Positioning of lead 10 may be aided by imaging techniques, such as fluoroscopy. In some embodiments, a plurality of stimulation leads may be provided. As will be described, lead 10 is coupled to an implantable neurostimulator either directly or via a lead extension.

In many instances, migration of lead 10, following implantation, can have detrimental effects on the quality of therapy delivered to a patient 12. For example, migration of lead 10 may cause displacement of electrodes carried by the lead to a target site. As a result, the electrodes may not be properly positioned to deliver the therapy, possibly undermining therapeutic efficacy. Fixating the neurostimulation lead 10 to surrounding tissue prevents lead migration, however, and can avoid harmful effects that may result from a loose neurostimulation lead 10.

To that end, the invention provides a lead 10 with a fixation mechanism (not shown in FIG. 1) to provide fixation between the lead 10 and tissue surrounding the lead 10, such as tissue within sacrum 16 in the example of FIG. 1. The fixation mechanism of the invention may permit only minimally invasive surgery, which allows for reduced pain and discomfort for the patient relative to surgery, as well as quicker recovery time. In some embodiments, the fixation mechanism may be an expandable member that expands radially outward from the lead body to contact surrounding tissue. The fixation mechanism may be selectively restrained from expansion, however, and deployed via a needle or other introducer. As will be described, the ability to restrain the fixation mechanism permits lead 10 to maintain a relatively small overall lead diameter during lead insertion via a needle, and then subsequently expand when the lead reaches the target stimulation site.

Figure 2:
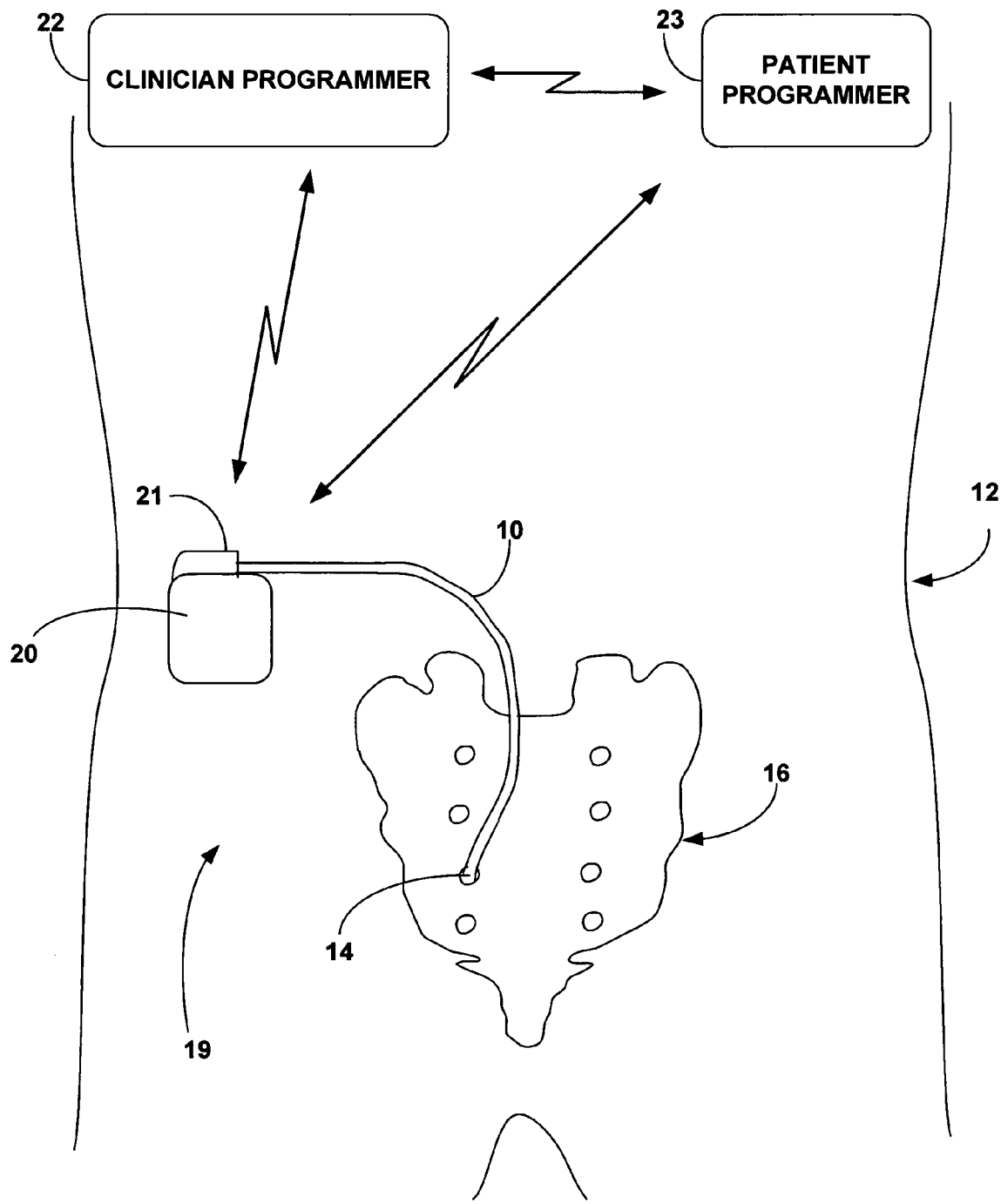
FIG. 2 is a diagram illustrating an implantable neurostimulation system for stimulating nerves, such as sacral nerves, via lead.

FIG. 2 is a diagram illustrating an implantable neurostimulation system 19 for stimulating a nerve, such as a sacral nerve, via lead 10. Neurostimulation system 19 delivers neurostimulation to the sacral nerves or other regions of the nervous system known to treat pelvic floor disorders, urinary control disorders, fecal control disorders, interstitial cystitis, sexual dysfunction, and pelvic pain. Again, system 19 and lead 10 may be useful in other neurostimulation applications, such as spinal cord stimulation, deep brain stimulation, gastric stimulation, and the like. As shown in FIG. 2, system 19 includes lead 10 and an implantable neurostimulator 20. In addition, a proximal end of stimulation lead 10 may be coupled to a connector block 21 associated with neurostimulator 20.

Neurostimulator 20 includes an implantable pulse generator, and delivers neurostimulation therapy to patient 12 in the form of electrical pulses generated by the implantable pulse generator. In the example of FIG. 2, neurostimulator 20 is implanted in the upper left buttock of patient 12, but may be implanted at other locations.

Lead 10 carries one or more of stimulation electrodes, e.g., 1 to 8 electrodes, to permit delivery of electrical stimulation to sacral nerves. For example, implantable neurostimulation system 19 may stimulate organs involved in urinary, fecal or sexual function via C-fibers or sacral nerves at the second, third, and fourth sacral nerve positions, commonly referred to as S2, S3, and S4, respectively. Also, in some embodiments, lead 10 may carry one or more sense electrodes to permit neurostimulator 20 to sense electrical signals within sacrum 16, if desired.

Lead 10 includes an outer lead body defining an inner lumen that contains one or more conductors to electrically couple the electrodes to terminals within neurostimulator 20, as shown in FIG. 2. In some embodiments, neurostimulator 20 may be coupled to two or more leads deployed at different positions, e.g., relative to the spinal cord or sacral nerves.

As mentioned above, migration of lead 10 can have detrimental effects on the efficacy of neurostimulation therapy for a patient 12. Fixating the neurostimulation lead 10 to surrounding tissue may prevent harmful effects that may result from a loose neurostimulation lead 10. However, suture-based fixation techniques typically require surgical implantation. As described below, a fixation mechanism (not shown in FIGS. 1 and 2) may provide fixation between the lead 10 and tissue surrounding the lead 10, such as sacrum 16, without the need for surgical implantation techniques.

As further shown in FIG. 2, implantable neurostimulation system 19 also may include a clinician programmer 22 and a patient programmer 23. Clinician programmer 22 may be a handheld computing device that permits a clinician to program neurostimulation therapy for patient 12, e.g., using input keys and a display. For example, using clinician programmer 22, the clinician may specify neurostimulation parameters for use in delivery of neurostimulation therapy.

Clinician programmer 22 supports radio frequency telemetry with neurostimulator 20 to download neurostimulation parameters and, optionally, upload operational or physiological data stored by neurostimulator. In this manner, the clinician may periodically interrogate neurostimulator 20 to evaluate efficacy and, if necessary, modifies the stimulation parameters.

Like clinician programmer 22, patient programmer 23 may be a handheld computing device. Patient programmer 23 may also include a display and input keys to allow patient 12 to interact with patient programmer 23 and implantable neurostimulator 20. In this manner, patient programmer 23 provides patient 12 with an interface for control of neurostimulation therapy by neurostimulator 20.

For example, patient 12 may use patient programmer 23 to start, stop or adjust neurostimulation therapy. In particular, patient programmer 23 may permit patient 12 to adjust stimulation parameters such as duration, amplitude, pulse width and pulse rate, within an adjustment range specified by the clinician via clinician programmer 22.

Neurostimulator 20, clinician programmer 22 and patient programmer 23 may communicate via wireless communication, as shown in FIG. 2. Clinician programmer 22 and patient programmer 23 may, for example, communicate via wireless communication with neurostimulator 20 using RF telemetry techniques known in the art. Clinician programmer 22 and patient programmer 23 also may communicate with each other using any of a variety of local wireless communication techniques, such as RF communication according to the 802.11 or Bluetooth specification sets, or other standard or proprietary telemetry protocols.

Figure 3:
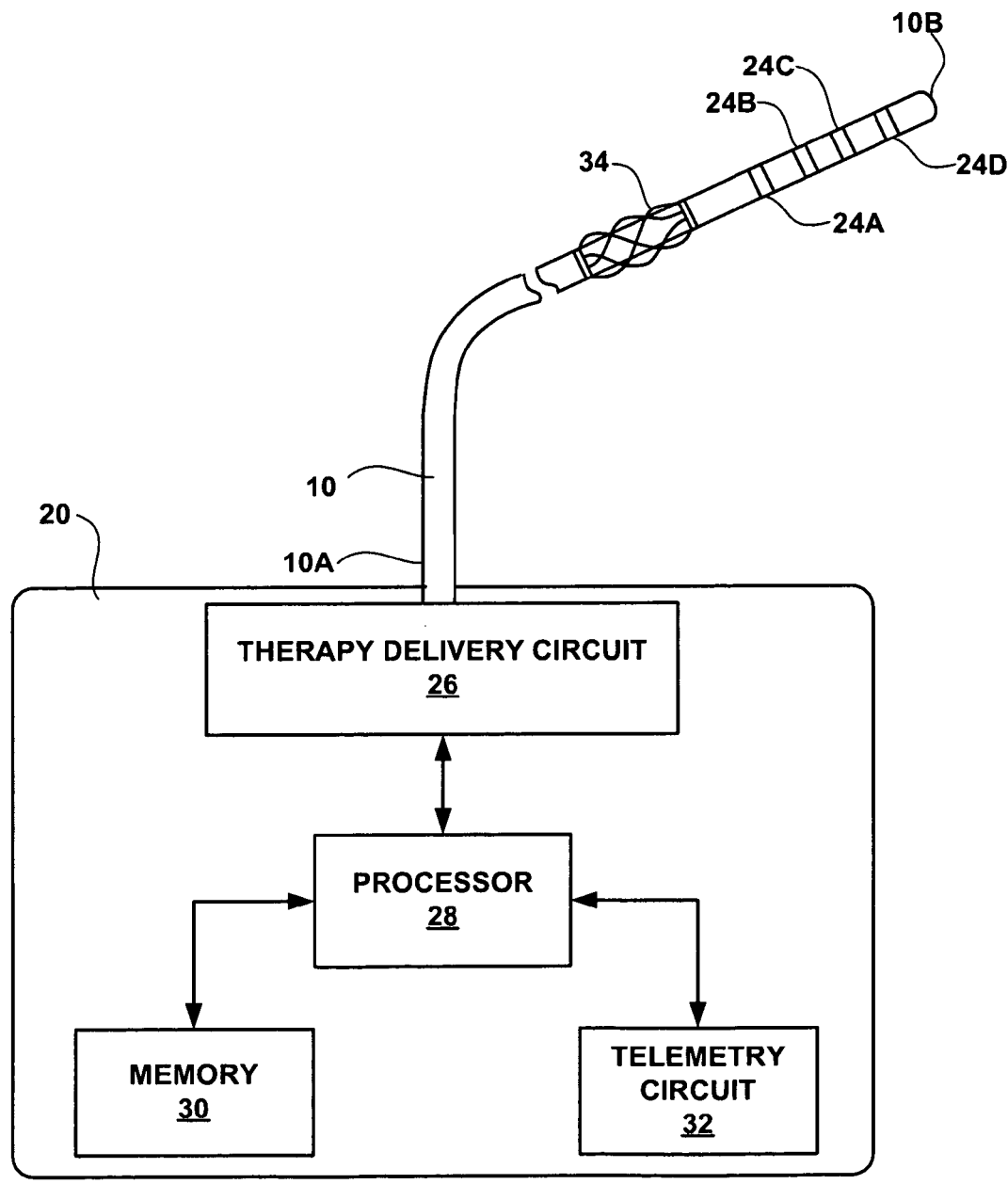
FIG. 3 is a block diagram illustrating various components of an implantable neurostimulator with an implantable lead incorporating a fixation mechanism.

FIG. 3 is a block diagram illustrating various components of an implantable neurostimulator 20 incorporating an implantable lead 10 with a fixation mechanism 34. As shown in FIG. 3, neurostimulator 20 delivers neurostimulation therapy via electrodes 24A, 24B, 24C, 24D of lead 10 (collectively "electrodes 24"). In some embodiments, electrodes 24 may be ring electrodes. The configuration, type and number of electrodes 24 illustrated in FIG. 3 are merely exemplary. Electrodes 24 are electrically coupled to a therapy delivery circuit 26 via conductors within lead 10. Therapy delivery circuit 26 may, for example, include an implantable pulse generator coupled to a power source such as a battery. The implantable pulse generator within therapy delivery circuit 26 delivers electrical pulses to patient 12 via at least some of electrodes 24 under the control of a processor 28.

Processor 28 controls the implantable pulse generator within therapy delivery circuit 26 to deliver neurostimulation therapy according to selected stimulation parameters. Specifically, processor 28 controls therapy delivery circuit 26 to deliver electrical pulses with selected amplitudes, pulse widths, and rates specified by the programs. In addition, processor 28 also controls therapy delivery circuit 26 to deliver the neurostimulation pulses via selected subsets of electrodes 24 with selected polarities.

Processor 28 may control therapy delivery circuit 26 to deliver each pulse according to a different program, thereby interleaving programs to simultaneously treat different symptoms or provide a combined therapeutic effect. For example, in addition to treatment of one symptom such as sexual dysfunction, neurostimulator 20 may be configured to deliver neurostimulation therapy to treat other symptoms such as pain or incontinence. Processor 28 may include a microprocessor, a controller, a DSP, an ASIC, an FPGA, discrete logic circuitry, or the like.

Neurostimulator 20 also includes a memory 30. In some embodiments, memory 30 stores multiple sets of stimulation parameters that are available to be selected by patient 12 for delivery of neurostimulation therapy. For example, memory 30 may store stimulation parameters transmitted by clinician programmer 22.

Memory 30 also stores program instructions that, when executed by processor 28, cause neurostimulator 20 to deliver neurostimulation therapy. Memory 30 may include any volatile or non-volatile media, such as a RAM, ROM, CD-ROM, NVRAM, EEPROM, flash memory, and the like. Accordingly, computer-readable media storing instructions may be provided to cause processor 28 to provide functionality as described herein.

A telemetry circuit 32 supports wireless communication between neurostimulator 20, clinician programmer 22, and patient programmer 23. In addition, in some embodiments, telemetry circuit 32 supports wireless communication with one or more wireless sensors that sense physiological signals and transmit the signals to neurostimulator 20.

As described above, a fixation mechanism 34 may be mounted to lead 10 to fixate the lead to any tissue surrounding the lead, such as tissue within an epidural region or tissue within or near a foramen 14 of sacrum 16. Fixation mechanism 34 may be mounted between electrodes 24 at a distal end of lead 10 and a proximal end of the lead. In particular, fixation mechanism 34 may be disposed adjacent electrodes 24 near the distal end of lead 10 in order to fix the electrodes in place relative to a target stimulation site. Also, as illustrated in FIG. 3, fixation mechanism 34 may be axially displaced (along the longitudinal axis measured from proximal end 10A of lead 10 to distal end 10B of lead 10) from electrodes 24. In this manner, fixation mechanism 34 may be positioned at a location on lead 10 that is physically distinct from that of electrodes 24.

In accordance with an embodiment of the invention, fixation mechanism 34 may include one or more expandable wire-like elements, which may be configured in a substantial helical shape or other shapes. The material of the wire-like elements may have elastic or super-elastic properties. In one embodiment, the material of the wire-like elements may be a shape memory alloy, such as Nitinol.

In one embodiment, for sacral applications, fixation mechanism 34 may be approximately sized to be expandable to a diameter sufficient to fix lead 10 within tissue site posterior to foramen 14. Alternatively, fixation mechanism 34 may facilitate fixation of lead 10 within other tissues target sites, including the epidural region proximate the spine. In those cases, fixation mechanism 34 may be sized to expand to any of a variety of diameters appropriate for engagement of tissue within the desired target site.

Figure 4A:
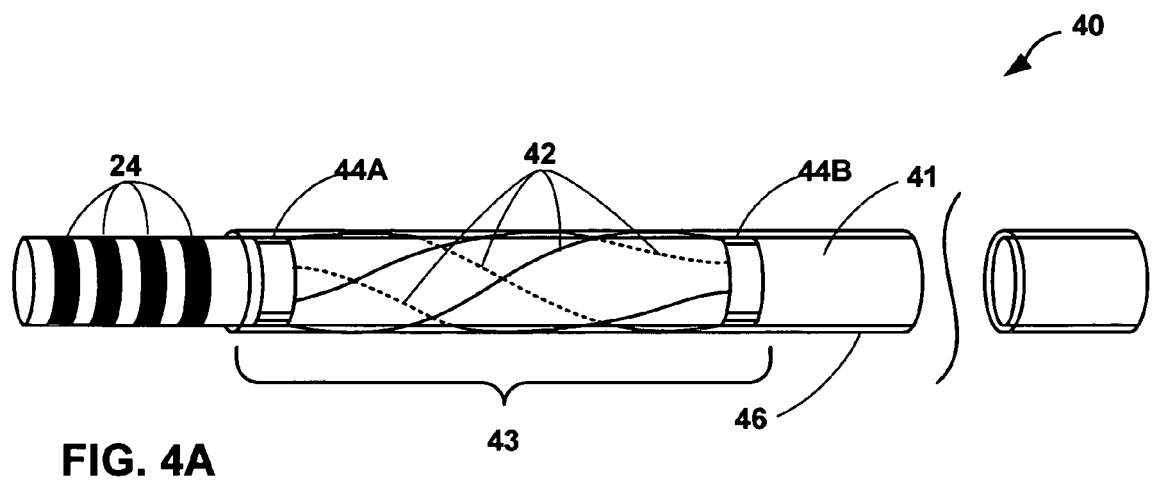
FIG. 4A is a perspective drawing illustrating an exemplary neurostimulation lead that may be fixated to surrounding tissue.

FIG. 4A is a perspective drawing illustrating an exemplary neurostimulation lead 40 that may be fixated to surrounding tissue to avoid lead migration following implantation. As shown in FIG. 4A, neurostimulation lead 40 includes a lead body 41, a plurality of stimulation electrodes 24, and a fixation mechanism 43, which includes one or more expandable wire-like elements 42. In this example, fixation mechanism 43 includes a plurality of wire-like elements 42. Dotted lines are used to indicate the parts of wire-like elements 42 that are behind lead body 41.

In one embodiment, wire-like elements 42 may be configured in a substantial helical shape. As shown in FIG. 4A, fixation mechanism 43 includes four wire-like elements 42, each having a substantial helical shape. The material of the wire-like elements may include elastic or super-elastic properties. In one embodiment, the material of the wire-like elements may include a shape memory alloy, such as Nitinol.

Proximal ends and distal ends of wire-like elements 42 may be mounted to lead body 41 by a variety of techniques. In one embodiment, retainer rings 44A and 44B (collectively retainer rings 44) may be mounted about the lead body to retain opposite ends of wire-like elements 42. Lead body 41 and retainer rings 44 may include polyurethane or silicone in some embodiments. Alternatively, retainer rings 44 may be formed from a metal in some embodiments. In other embodiments, adhesive bonding, crimping, welding, and the like may be used to secure wire-like elements 42 to lead body 41. The points where the wire-like elements are secured to lead body 41 may be referred to as proximal joints and distal joints. In one embodiment, the distal joint may be weaker than the proximal joint. This feature, which will be described in more detail below, may be useful when withdrawing neurostimulation lead 40 for explant. In particular, the weakened distal joint may facilitate withdrawal even when there is significant fibrous ingrowth near neurostimulation lead 40 by promoting breakage of the lead.

In practice, fixation mechanism 43 facilitates fixation of neurostimulation lead 40 to surrounding tissue, e.g., within or posterior to foramen 14. Fixation mechanism 43 may be sized to be expandable to a diameter sufficient to fixate lead 40 within a target site. For example, fixation mechanism may be expandable to a diameter in a range of approximately 2 mm to 10 mm, and more preferably 4 to 6 mm, when disposed within a tissue site proximate the foramen 14 in the presence of compressive forces generated by typical tissue. In another embodiment, fixation mechanism 43 may facilitate fixation of neurostimulation lead 40 to tissue surrounding neurostimulation lead 40 in other target sites. If lead 40 is implanted in the epidural region around the spine, for example, fixation mechanism 43 may be expandable to a diameter in a range of approximately 6 mm to 15 mm, and more preferably 9 mm to 12 mm. Also, if fixation mechanism 43 is spring-biased, it may have a different spring force depending on the known tissue characteristics of the intended target site for implantation, e.g., tissue presented by sacral, spinal cord, gastric, deep brain or other stimulation sites. As an example, the epidural region may present less resistance to expansion that more dense tissue area in other areas.

As described above, neurostimulation lead 40 carries a number of stimulation electrodes 24 to permit delivery of electrical stimulation to a target stimulation site such as the sacral nerves. In one embodiment, stimulation electrodes 24 may include at least one electrode. Accordingly, lead body of neurostimulation lead 40 includes one or more conductors to electrically couple the electrodes 24 to terminals within neurostimulator 20, as shown in FIG. 2. In one embodiment, the material of one of wire-like elements 42 may allow the wire-like element to act as an electrode for neurostimulator 20, either as an anode or cathode.

Fixation mechanism 43 is shown in a restrained state in FIG. 4A. In particular, a restraint mechanism is shown restraining the expandable fixation mechanism 43 against expansion. For example, the restraint mechanism shown in FIG. 4A includes a lead introducer 46, or sheath, which defines an inner lumen that is sized to accommodate stimulation lead body 41 and fixation mechanism 43. When fixation mechanism 43 is within lead introducer 46, the lead introducer 46 encloses the fixation mechanism and forces the fixation mechanism into a compressed state. Restraining fixation mechanism 43 permits lead introducer 46 and stimulation lead 10 to retain a small overall lead diameter during lead implantation. In this manner, the fixation mechanism 43 may be restrained from expansion and may be deployed via a needle or other minimally invasive delivery device. Introducing the fixation mechanism 43 via a needle requires only minimally invasive techniques, which allows for quicker recovery time.

In one embodiment, at least a portion of neurostimulation lead 40, such as lead body 41, may include radio-opaque material that is detectable by imaging techniques, such as fluoroscopic imaging. This feature may be helpful for maneuvering neurostimulation lead 40 relative to a target site within the body. For example, the distal end of neurostimulation lead 40 may include radio-opaque material that is visible via fluoroscopic imaging. A physician may use the imaging during the introduction and withdrawal of neurostimulation lead 40.

Figure 4B:
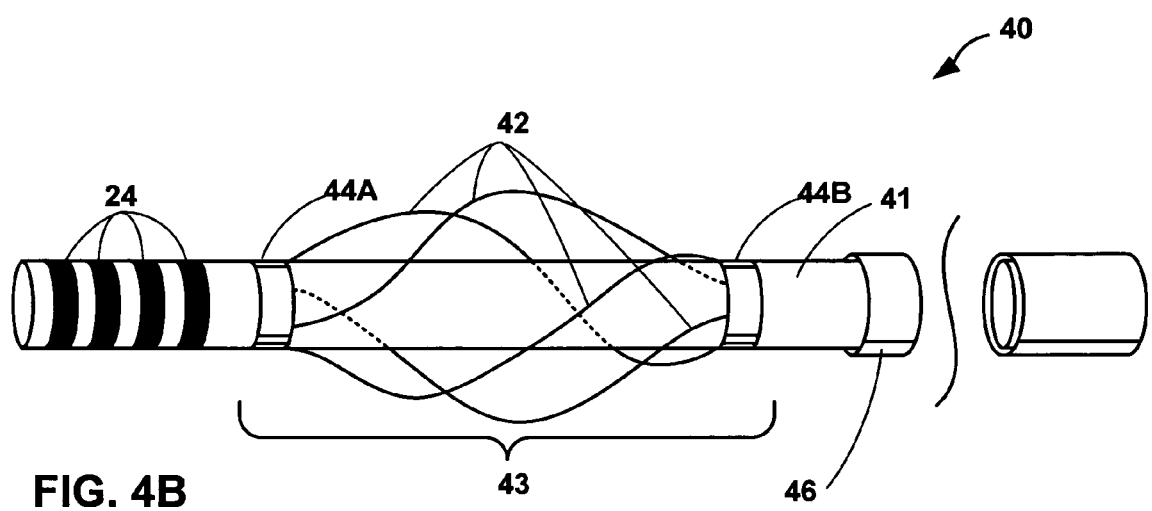
FIG. 4B is a perspective drawing illustrating an exemplary neurostimulation lead that is expanded for fixating the neurostimulation lead to surrounding tissue.

FIG. 4B is a perspective drawing illustrating an exemplary neurostimulation lead 40 with fixation mechanism 43 expanded for fixating the neurostimulation lead to surrounding tissue. The restraint mechanism, which may be a lead introducer 46, is shown partially withdrawn from lead body 41. Withdrawing the restraint mechanism exposes fixation mechanism 43 and allows wire-like elements 42 to expand radially outward from the lead body 41. Wire-like elements 42 expand outward in response to spring force provided by the elastic or superelastic properties of the elements. In one embodiment, the diameter of fixation mechanism 43 may be expandable to approximately 2 mm to 10 mm, and more preferably 4 to 6 mm. In another embodiment, the diameter of fixation mechanism 43 may be expandable to a larger diameter, e.g., for epidural implantation. The larger diameter may be approximately 6 mm to 15 mm, and more preferably 9 mm to 12 mm, as discussed above.

Figure 5A:
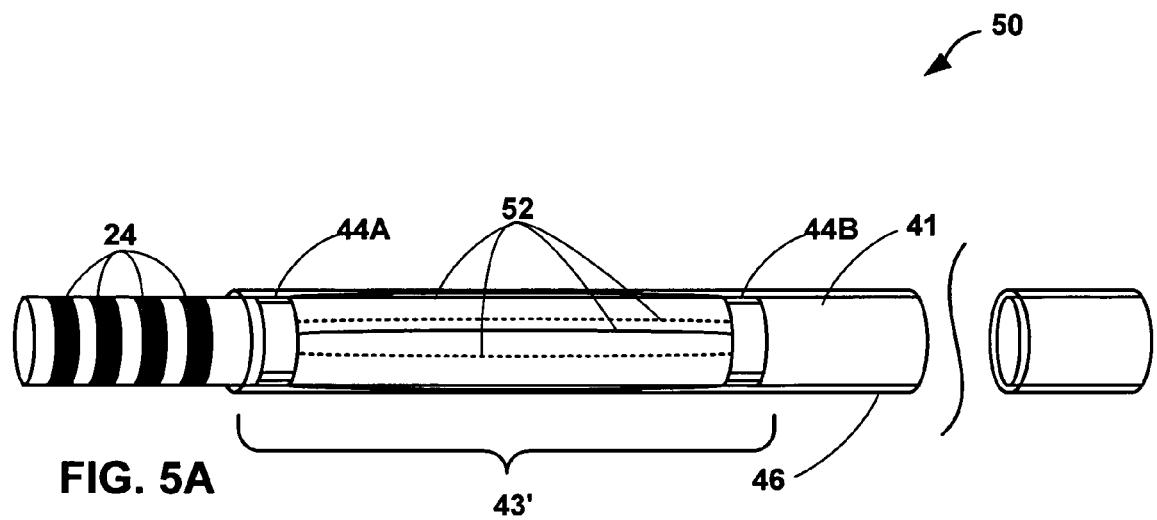
FIG. 5A is a perspective drawing illustrating an alternate neurostimulation lead that may be fixated to surrounding tissue.

FIG. 5A is a perspective drawing illustrating an alternate neurostimulation lead 50 with an alternative fixation mechanism 43' that may be fixated to surrounding tissue. Fixation mechanism 43' of FIG. 5A is similar to fixation 43 of FIGS. 4A and 4B, but has a different shape. As shown in FIG. 5A, wire-like elements 42 of fixation mechanism 43 are restrained by restraint mechanism 46, which may be a lead introducer. Dotted lines are used to indicate the parts of wire-like elements 42 that are behind lead body 41. Again, neurostimulation lead 50 is very similar to neurostimulation lead 40, with the main difference being the configuration of wire-like elements 52.

In particular, in the example of FIG. 5A, wire-like elements 52 do not cross each other as they did in the helical configuration of wire-like elements 42 in FIG. 4A. Instead, FIG. 5A shows four wire-like elements with ends that are distributed around lead body 41 in a substantially even manner. Wire-like elements 52 may be configured in a variety of other designs. For example, there may be any number of wire-like elements 52. In addition, the wire-like elements 52 may be distributed unevenly around lead body 41. In one embodiment, wire-like elements 52 may extend from only one side of lead body 41, rather than being distributed about the circumference of the lead body.

Figure 5B:
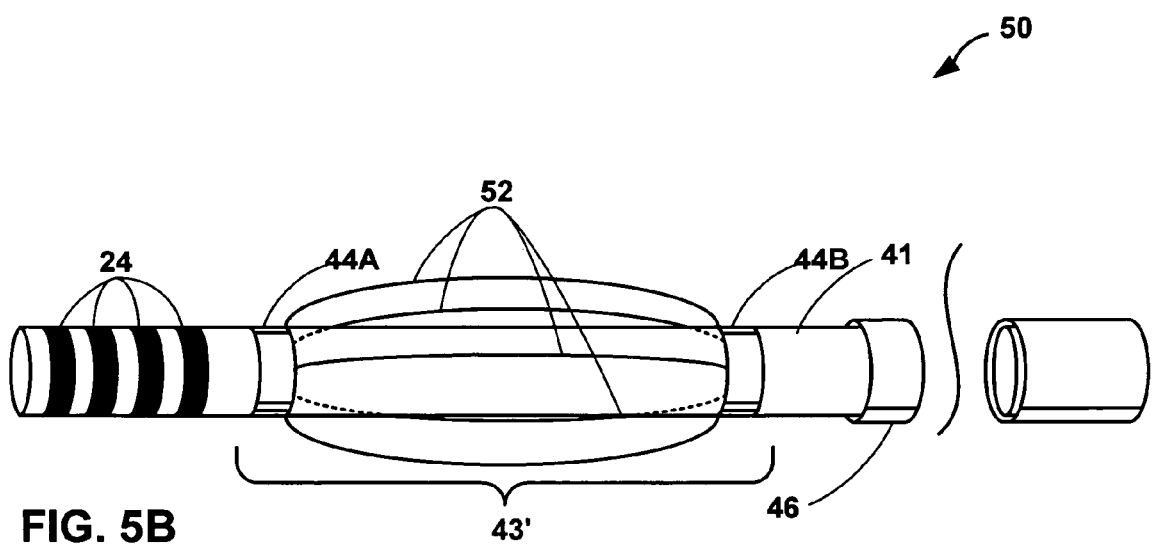
FIG. 5B is a perspective drawing illustrating an exemplary neurostimulation lead that is expanded for fixating the neurostimulation lead to surrounding tissue.

FIG. 5B is a perspective drawing illustrating an exemplary neurostimulation lead 52 with fixation mechanism 43' expanded for fixating the neurostimulation lead to surrounding tissue. The restraint mechanism, which may be a lead introducer 46, is shown partially withdrawn from lead body 41. Withdrawing the restraint mechanism allows wire-like elements 42 to expand. In one embodiment, the diameter of fixation mechanism 43' may be expandable to approximately 2 mm to 10 mm, and more preferably 4 mm to 6 mm, for implantation within a tissue site. In another embodiment, for epidural fixation, the diameter of fixation mechanism 43' may be expandable to a larger diameter on the order of approximately 6 mm to 15 mm, and more preferably approximately 9 to 12 mm.

Figure 6A:
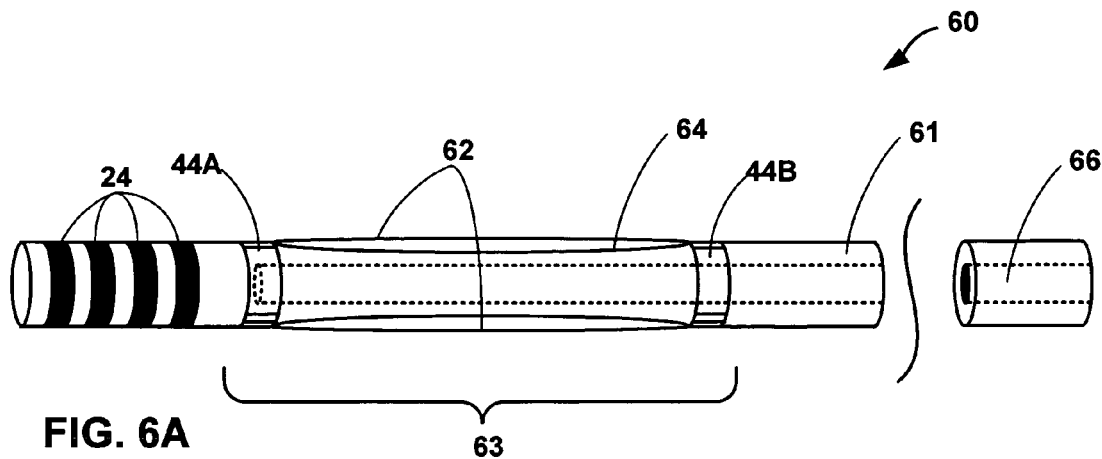
FIG. 6A is a perspective drawing illustrating an alternate neurostimulation lead that may be fixated to surrounding tissue.

FIG. 6A is a perspective drawing illustrating an alternate neurostimulation lead 60 that may be fixated to surrounding tissue. As shown in FIG. 6A, neurostimulation lead 60 includes a lead body 61, one or more stimulation electrodes 24, and an alternative fixation mechanism 63, which includes a number of expandable wire-like elements 62. Dotted lines are used to indicate the parts of wire-like elements 62 that are behind lead body 41 in FIG. 6A. As described above, fixation mechanism 63 may be mounted to lead 10 to fixate the lead to any tissue surrounding the lead, such as tissue posterior to foramen 14 of sacrum 16.

The wire-like elements 62 of neurostimulation lead 60 may come in many configurations. As shown in FIG. 6A, two uncrossed wire-like elements 62 may be included in the neurostimulation lead 60. Additionally, the wire-like elements 62 of expansion mechanism 63 may be configured in a substantial helical shape in some embodiments. In addition, fixation mechanism 63 may include retainer rings 44A and 44B (collectively "retainer rings 44").

Lead body 61 of neurostimulation lead 60 is shown with an inner lumen that accommodates a restraint mechanism, such as a stylet 66. A distal end of stylet 66 bears against a surface within lead body 61 to exert a linear force along the length of the lead body and cause the lead body to straighten out. In some embodiments, lead body 61 may include at least a portion that is formed from an elastic material, causing the diameter of the lead body portion to decrease when the portion is stretched. The elastic portion 64 of the lead body 61 is shown in FIG. 6A in a restrained state, where the diameter of the stretched elastic portion is smaller than the portion of the lead body that is not stretched.

Stretching the lead body 61 allows wire-like elements 62 to lengthen and straighten out, as shown in FIG. 6A. In other words, wire-like elements 62 of fixation mechanism 63 may be restrained from expansion by straightening lead body 61. In some embodiments, an elastic portion 64 of lead body 61 may be provided and stretched under axial force from stylet 66, thereby lengthening the linear distance between ends of wire-like elements 62. Relaxing the elastic portion 64 of lead body 61, e.g., by retracting the stylet 66, causes lead body to decrease in length, permitting wire-like elements 62 to extend radially outward from the lead body, as shown in FIG. 6B.

Restraining fixation mechanism 63 by extension of stylet 66 allows for relatively large stimulation zones while still retaining a small overall lead diameter during lead deployment. As in the embodiment of FIGS. 4 and 5, the fixation mechanism 63 of FIG. 6A may be restrained from expansion and may be deployed via a needle. Introducing the lead body 61 and fixation mechanism 63 via a needle requires only minimally invasive techniques, rather than surgery.

Figure 6B:
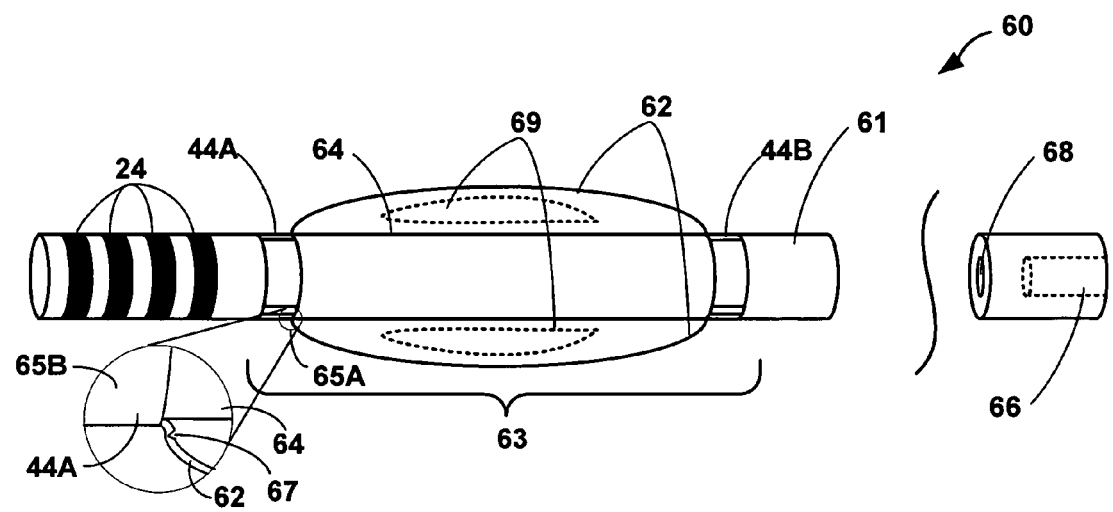
FIG. 6B is a perspective drawing illustrating an alternate neurostimulation lead that is expanded for fixing the neurostimulation lead to surrounding tissue.

FIG. 6B is a perspective drawing illustrating neurostimulation lead 60 of FIG. 6A with fixation mechanism 63 expanded for fixating the neurostimulation lead to surrounding tissue. A restraint mechanism, which may be stylet 66, is shown partially withdrawn from lead body 61. Withdrawing the restraint mechanism 66 from the inner lumen 68 of lead stimulator 60 allows wire-like elements 62 to expand. In particular, stylet 66 may initially extend lead body straight so that wire-like elements 62 are also pulled straight and are restrained against expansion. In some embodiments, stylet 66 may exert axial force along the longitudinal axis of lead body 61 to thereby stretch at least a portion of the lead body. Upon withdrawal of stylet 66, spring force exerted by wire-like elements 62 causes the wire-like elements to expand radially outward. Again, the diameter of fixation mechanism 63 may be expandable to range of diameters appropriate for different target sites, as described above.

After neurostimulation lead 60 has been implanted within a patient for a considerable amount of time, fibrous ingrowth 69 may develop around neurostimulation lead 60. Resistance may be encountered if withdrawal of neurostimulation lead 60 for explant is attempted. An embodiment of the invention may provide a feature to reduce resistance and to limit further problems due to the fibrous ingrowth 69.

Figure 6C:
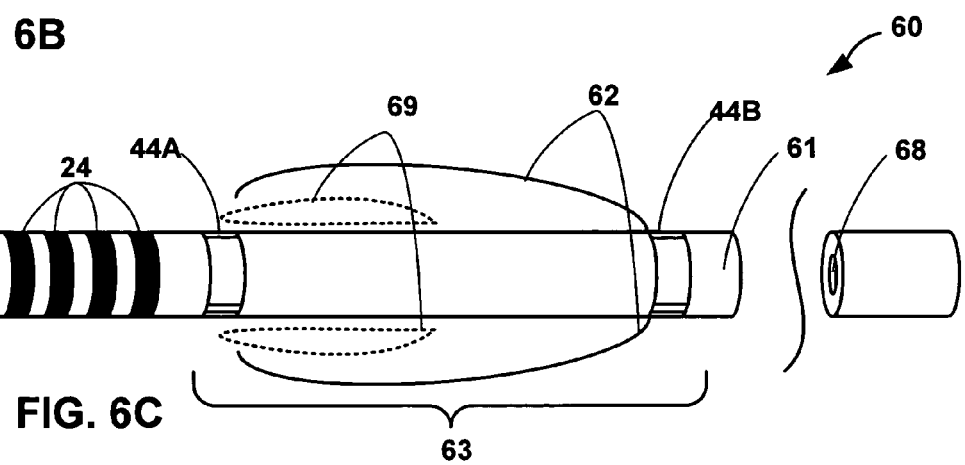
FIG. 6C is a perspective drawing illustrating a technique for limiting the effects of fibrous ingrowth near a neurostimulation lead upon explant.

FIG. 6C is a perspective drawing illustrating a technique for limiting the effects of fibrous ingrowth 69 near an exemplary neurostimulation lead 60. As described above, the points where wire-like elements 62 are secured to lead body 61 may be referred to as proximal joints and distal joints. In one embodiment, the distal joint may be intentionally made weaker than the proximal joint. Circle 65B provides an enlarged representation of circle 65A. As shown in the enlarged view, the distal joint of wire-like element 62 may be intentionally thinned to create a breakpoint that causes wire-like element 62 to break under sufficient force. For example, the distal joint may be engineered to be weaker than the proximal joint by perforating, scoring, thinning, or otherwise working the distal joint to break away under force generated by withdrawal of lead 60 from a target site.

This feature may be useful when withdrawing neurostimulation lead 40 from fibrous ingrowth 69. In practice, the relatively weak distal joints of wire-like elements 62 may disconnect from lead body 61, while the relatively strong proximal joints of wire-like elements 62 may remain connected to lead body 61. With distal joints of wire-like elements 62 disconnected, neurostimulation lead 60 may be withdrawn from the patient, leaving fibrous ingrowth 69 behind.

If there is no substantial fibrous ingrowth 69, it may be possible to withdraw neurostimulation lead by simply restraining fixation mechanism 63 (as in FIG. 6A), i.e., returning the fixation mechanism from its expanded configuration to it restrained configuration, which may serve to loosen neurostimulation lead 60 from its fixated state.

Figure 7:
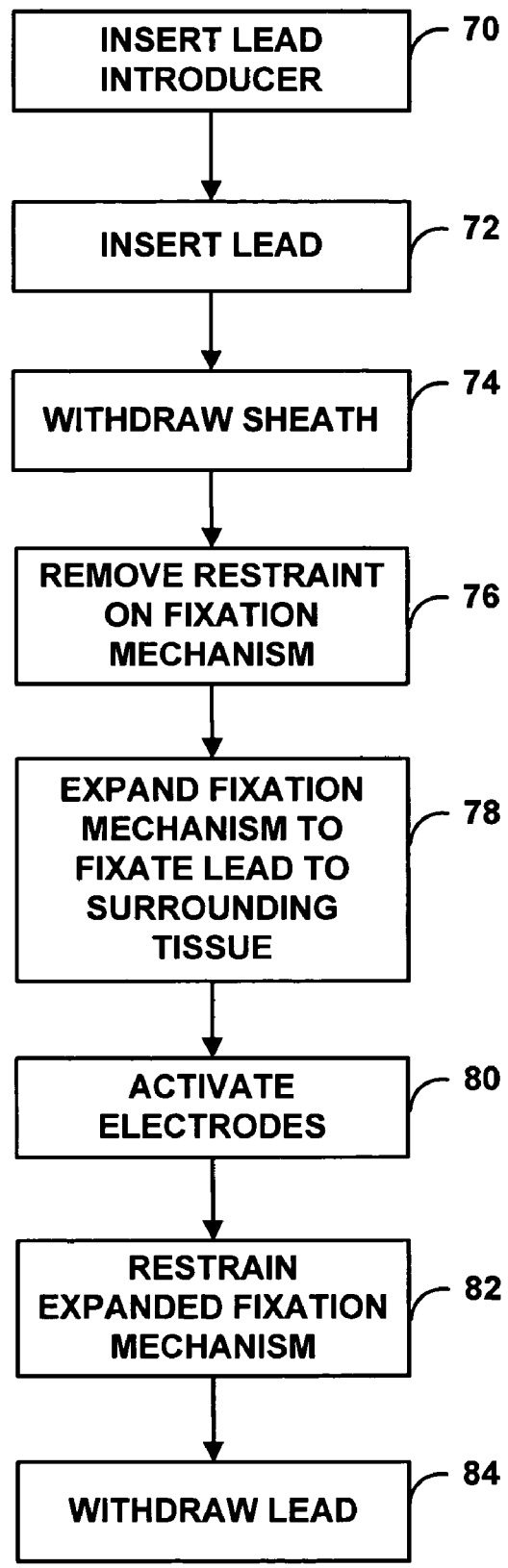
FIG. 7 is a flow diagram illustrating implantation and use of an implantable neurostimulator system.

FIG. 7 is a flow diagram illustrating implantation and use of an implantable neurostimulator system. An exemplary technique for percutaneously implanting a neurostimulation lead by using a lead introducer 30 is described herein. Initially, a needle assembly is inserted into a patient. The needle assembly may include a needle and an introducer stylet fitted into a lumen defined by the needle. The lumen may have a diameter between 14 and 20 gauge to allow the needle to receive the introducer stylet. The introducer stylet may fill the lumen of the needle, preventing tissue coring. In some instances, the needle may include a straight needle for sacral implantation or a modified Tuohy needle for epidural applications, which has an opening that is angled approximately 45 degrees so that an instrument passing through the needle exits at an angled.

The neurostimulation lead introducer may be inserted (70) by a variety of techniques not limited to the technique described above. The neurostimulation lead is inserted (72) into the patient and advances through the lead introducer. The neurostimulation lead advances until it reaches the therapy target site. Meanwhile, a restraint mechanism, such as the lead introducer, a sheath other than the lead introducer, a stylet, or the like, restrains expansion of the expandable fixation mechanism that is part of the neurostimulation lead to prevent radial expansion The fixation mechanism includes wire-like elements, as described herein, that are expandable to fix the neurostimulator lead to surrounding tissue at a tissue target site. Once the neurostimulation lead reaches the therapy target site, the lead introducer is withdrawn (74).

In one embodiment, the restraint mechanism includes the lead introducer. In this case, the act of withdrawing the lead introducer removes the restraint on a fixation mechanism (76). In another embodiment, the restraint mechanism includes a stylet that may extend through a lumen of the neurostimulation lead, causing part of the lead to straighten, lengthen or stretch, and allowing the wire-like elements of the fixation mechanism to be restrained against the body of neurostimulation lead. In this case, removing the stylet, which acts as a restraint mechanism, removes the restraint on a fixation mechanism (76).

After the neurostimulation lead has been properly placed in a therapy target site, restraint mechanism is removed from the fixation mechanism, allowing the wire-like elements to expand. The expansion of the wire-like elements fixates the neurostimulation lead to surrounding tissue (78), e.g., in an epidural region proximate the spine or a sacral foramen. Fixating the neurostimulation lead to surrounding tissue may prevent harmful behavior that may result from a loose neurostimulation lead.

The electrodes on the neurostimulation lead may be activated (80) to provide therapy to the patient, e.g., by coupling a proximal end of neurostimulation lead to a neurostimulator. In one embodiment, a lead extension may be provided to couple the neurostimulation lead to the neurostimulator.

Therapy may require that the neurostimulation lead be activated for only a short period of time, e.g., for trial stimulation, sometimes referred to as screening. On the other hand, therapy may require that the neurostimulation lead be implanted chronically for a number of years. In either case, it may become necessary to remove the neurostimulation lead from the patient. The expanded fixation mechanism may be restrained as it was when it was inserted (82), and the neurostimulation lead may be withdrawn (84). As described above, it may be helpful to disconnect the distal joints of the wire-like elements. This feature may be useful when withdrawing the neurostimulation lead from fibrous ingrowth. In practice, the relatively weak distal joints of wire-like elements 62 may disconnect from the lead body, while the relatively strong proximal joints of the wire-like elements may remain connected to the lead body. With distal joints of wire-like elements disconnected, the neurostimulation lead may be withdrawn from the patient, leaving fibrous ingrowth behind.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems and leads for neurostimulation, as described herein. Also, the leads described herein may have a variety of neurostimulation applications, as well as possible applications in other electrical stimulation contexts, such as delivery of cardiac electrical stimulation, including paces, pulses, and shocks.

In addition, although the embodiments described herein generally contemplate a fixation mechanism that extends outward from the lead body along multiple radii about the lead body circumference, it is conceivable that the lead body may carry one or more wire-like elements that extend outward from only one side of the lead body, or from less than all sides. Also, it is conceivable that a wire-like element in accordance with the invention may be appropriately formed in a helical configuration such that portions of the wire-like element extend about all or substantially all of the entire circumference of the lead body, and thereby extend outward on all of substantially all sides of the lead body.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:

1. A neurostimulation lead comprising:
   a lead body having a proximal end and a distal end, and defining a longitudinal axis;
   a plurality of stimulation electrodes disposed adjacent the distal end of the lead body; and
   a fixation mechanism mounted to the lead body at a position between one of the electrodes and the proximal end of the lead body, the fixation mechanism including one or more wire-like elements that are expandable to fix the lead body at a tissue target site, wherein the position is axially displaced from the plurality of stimulation electrodes, and wherein proximal and distal ends of each of the one or more wire-like elements are mechanically coupled to the lead body, and, for each of the one or more wire-like elements, the proximal and distal ends of the wire-like element are axially displaced from each other along the longitudinal axis of the lead body.

2. The neurostimulation lead of claim 1, wherein each of the wire-like elements includes an elastic material.

3. The neurostimulation lead of claim 1, each of the wire-like elements having a proximal joint where the proximal end of the wire-like element meets the lead body, and a distal joint where the distal end of the wire-like element meets the lead body, wherein the distal joint is weaker than the proximal joint.

4. The neurostimulation lead of claim 1, wherein each of the wire-like elements includes a shape memory alloy.

5. The neurostimulation lead of claim 1, wherein each of the wire-like elements includes a super-elastic material.

6. The neurostimulation lead of claim 1, further comprising an inner lumen to accommodate a stylet.

7. The neurostimulation lead of claim 1, further comprising a restraint mechanism to restrain the wire-like elements against expansion, wherein the wire-like elements expand upon removal of at least part of the restraint mechanism.

8. The neurostimulation lead of claim 7, wherein the restraint mechanism includes a lead introducer, the lead introducer defining a lead introducer lumen sized to accommodate the stimulation lead body.

9. The neurostimulation lead of claim 7, wherein the restraint mechanism includes a stylet, the stylet accommodated by an inner lumen of the neurostimulation lead.

10. The neurostimulation lead of claim 1, wherein at least a portion of the lead body is elastic, causing a diameter of the lead body portion to decrease when the lead body portion is stretched.

11. The neurostimulation, lead of claim 1, wherein each of the wire-like elements is configured in a substantial helical shape.

12. The neurostimulation lead of claim 1, further comprising retainer rings mounted about the lead body to retain opposite ends of each of the wire-like elements.

13. The neurostimulation lead of claim 1, wherein one of the wire-like elements acts as an electrode for neurostimulation current.

14. The neurostimulation lead of, claim 1, wherein the plurality of electrodes include at least four electrodes.

15. The neurostimulation lead of claim 1, wherein the fixation mechanism is sized to be expandable to a diameter in a range of approximately 2 to 10 mm.

16. The neurostimulation lead of claim 1, wherein the fixation mechanism is sized to be expandable to a diameter in a range of approximately 4 to 6 mm.

17. The neurostimulation lead of claim 1, wherein the fixation mechanism is sized to be expandable to a diameter in a range of approximately 6 to 15 mm.

18. The neurostimulation lead of claim 1, wherein the fixation mechanism is sized to be expandable to a diameter in a range of approximately 9 to 12 mm.

19. The neurostimulation lead of claim 1, wherein the stimulation lead includes radio-opaque material that is detectable by fluoroscopic imaging.

20. The neurostimulation lead of claim 1, wherein the lead is one of a sacral lead, a pudendal nerve lead, and a spinal cord stimulation lead.

21. The neurostimulation lead of claim 1, wherein at least one of the electrodes comprises a ring electrode.

22. A neurostimulation system comprising:
   an implantable neurostimulation pulse generator;
   a lead body having a proximal end and a distal end, and defining a longitudinal axis;
   a plurality of stimulation electrodes disposed adjacent the distal end of the lead body;
   an electrical conductor to electrically couple the implantable neurostimulation energy generator to a number of the electrodes; and
   a fixation mechanism mounted to the lead body at a position between one of the electrodes and the proximal end of the lead body, the fixation mechanism including one or more wire-like elements that are expandable to fix the lead body at a tissue target site, wherein the position is axially displaced from the plurality of stimulation electrodes, and wherein proximal and distal ends of each of the one or more wire-like elements are mechanically coupled to the lead body, and, for each of the one or more wire-like elements, the proximal and distal ends of the wire-like element are axially displaced from each other along the longitudinal axis of the lead body.

23. The neurostimulation system of claim 22, wherein each of the wire-like elements includes an elastic material.

24. The neurostimulation system of claim 22, each of the wire-like elements having a proximal joint where the proximal end of the wire-like element meets the lead body, and a distal joint where the distal end of the wire-like element meets the lead body, wherein the distal joint is weaker than the proximal joint.

25. The neurostimulation system of claim 22, wherein each of the wire-like elements includes a shape memory alloy.

26. The neurostimulation system of claim 22, wherein each of the wire-like elements includes a super-elastic material.

27. The neurostimulation system of claim 22, further comprising an inner lumen to accommodate a stylet.

28. The neurostimulation system of claim 22, further comprising a restraint mechanism to restrain the wire-like elements against expansion, wherein the wire-like elements expand upon removal of at least part of the restraint mechanism.

29. The neurostimulation system of claim 28, wherein the restraint mechanism includes a lead introducer, the lead introducer defining a lead introducer lumen sized to accommodate the stimulation lead body.

30. The neurostimulation system of claim 28, wherein the restraint mechanism includes a stylet, the stylet accommodated by an inner lumen of the neurostimulation lead.

31. The neurostimulation system of claim 22, wherein at least a portion of the lead body is elastic, causing a diameter of the lead body portion to decrease when the lead body portion is stretched.

32. The neurostimulation system of claim 22, wherein each of the wire-like elements is configured in a substantial helical shape.

33. The neurostimulation system of claim 22, further comprising retainer rings mounted about the lead body to retain opposite ends of each of the wire-like elements.

34. The neurostimulation system of claim 22, wherein one of the wire-like elements acts as an electrode for neurostimulation current.

35. The neurostimulation system of claim 22, wherein the electrodes include at least four electrodes.

36. The neurostimulation lead of claim 22, wherein the fixation mechanism is sized to be expandable to a diameter in a range of approximately 2 to 10 mm.

37. The neurostimulation lead of claim 22, wherein the fixation mechanism is sized to be expandable to a diameter in a range of approximately 4 to 6 mm.

38. The neurostimulation lead of claim 22, wherein the fixation mechanism is sized to be expandable to a diameter in a range of approximately 6 to 15 mm.

39. The neurostimulation lead of claim 22, wherein the fixation mechanism is sized to be expandable to a diameter in a range of approximately 9 to 12 mm.

40. The neurostimulation system of claim 22, wherein the stimulation lead includes radio-opaque material that is detectable by fluoroscopic imaging.

41. The neurostimulation system of claim 22, wherein at least one of the electrodes comprises a ring electrode.

42. A method comprising:
inserting a lead introducer into a patient;
inserting a lead into the patient via the introducer, wherein the lead includes a lead body having a proximal end and a distal end, and defining a longitudinal axis, a plurality of stimulation electrodes disposed on the lead body, and a fixation mechanism mounted to the lead body at a position between one of the electrodes and the proximal end of the lead body, the position being axially displaced from the plurality of stimulation electrodes and the fixation mechanism including one or more wire-like elements that are expandable to fix the lead body at a tissue target site, wherein proximal and distal ends of each of the one or more wire-like elements are mechanically coupled to the lead body, and, for each of the one or more wire-like elements, the proximal and distal ends of the wire-like element are axially displaced from each other along the longitudinal axis of the lead body; and
removing a restraint mechanism on the fixation mechanism, thereby permitting the wire-like elements to expand.

43. The method of claim 42, wherein removing a restraint includes withdrawing at least part of a stylet from a lumen of the lead, thereby releasing the fixation mechanism to expand.

44. The method of claim 42, wherein removing a restraint includes withdrawing at least a portion of the lead introducer, thereby releasing the fixation mechanism to expand.

45. The method of claim 42, further comprising:
detaching a distal end of each wire-like element; and
withdrawing the lead from the target site.

46. The method of claim. 42, further comprising:
restraining the expanded fixation mechanism; and
withdrawing the lead from the target site.

47. The method of claim 42, wherein the restraint mechanism includes a lead introducer, the lead introducer defining a lead introducer lumen sized to accommodate the stimulation lead body.

48. The method of claim 42, wherein the fixation mechanism is sized to be expandable to .a diameter in a range of approximately 2 to 10 mm.

49. The method of claim 42, wherein the fixation mechanism is sized to be expandable to a diameter in a range of approximately 4 to 6 mm.

50. The method of claim 42, wherein the fixation mechanism is sized to be expandable to approximately a diameter in a range of approximately 6 to 15 mm.

51. The method of claim 42, wherein the fixation mechanism is Sized to be expandable to approximately a diameter in a range of approximately 9 to 12 mm.

52. The method of claim 42, wherein each of the wire-like elements includes an elastic material.

53. The method of claim 42, wherein inserting the lead into the patient via the introducer comprises advancing the lead through the introducer to the target tissue site within an epidural space or proximate to a sacral foramen.

54. A stimulation lead comprising:
a lead body having a proximal end and a distal end, and defining a longitudinal axis;
a plurality of stimulation electrodes disposed on the lead body; and
means for fixing the lead body relative to tissue proximate a tissue target site, wherein the fixing means includes one or more wire-like elements that are expandable to fix the lead body at the tissue target site, wherein the fixing means is mounted to the lead body at a position between one of the electrodes and the proximal end of the lead body, and the position is axially displaced from the plurality of stimulation electrodes, and wherein proximal and distal ends of each of the one or more wire-like elements are mechanically coupled to the lead body, and, for each of the one or more wire-like elements, the proximal and distal ends of the wire-like element are axially displaced from each other along the longitudinal axis of the lead body.

55. The lead of claim 54, wherein each of the wire-like elements includes an elastic material.

56. The lead of claim 54, each of the wire-like elements having a proximal joint where the proximal end of the wire-like element meets the lead body, and a distal joint where the distal end of the wire-like element meets the lead body, wherein the distal joint is weaker than the proximal joint.

57. The lead of claim 54, wherein each of the wire-like elements includes a shape memory alloy.

58. The lead of claim 54, wherein each of the wire-like elements includes a super-elastic material.

59. The lead of claim 54, further comprising means for restraining the wire-like elements against expansion, wherein the wire-like elements expand upon removal of at least part of the restraining means.

60. The lead of claim 54, wherein the lead is one of a sacral lead, a pudendal nerve lead, and a spinal cord stimulation lead.

61. The neurostimulation lead of claim 1, further comprising a plurality of retainer rings, wherein the retainer rings mount the wire-like elements to the lead body at proximal ends and distal ends of the wire-like elements.

62. The neurostimulation lead of claim 1, wherein the fixation mechanism is spring-biased.

63. The neurostimulation system of claim 31, wherein the stylet provides an axial force that stretches the elastic portion of the lead body to restrain the wire-like elements against expansion.

64. The neurostimulation system of claim 63, wherein the elastic portion of the lead body decreases in length upon removal of the stylet.

65. The lead of claim 54, wherein at least one of the electrodes comprises a ring electrode.

* * * * *

UNITED STATES PATENT AND TRADEMARK OFFICE
CERTIFICATE OF CORRECTION

PATENT NO. : 8,260,436 B2
APPLICATION NO. : 10/698291
DATED : September 4, 2012
INVENTOR(S) : Martin T. Gerber Page 1 of 1

It is certified that error appears in the above-identified patent and that said Letters Patent is hereby corrected as shown below:

In the Claims

<u>Claim 46, Column 16, line 15:</u> "The method of claim.42," should read -- The method of claim 42 --.

<u>Claim 48, Column 16, line 23:</u> "expandable to .a diameter" should read -- expandable to a diameter --.

<u>Claim 51, Column 16, line 31-32:</u> "mechanism is Sized to be" should read -- mechanism is sized to be --.

Signed and Sealed this
Third Day of March, 2015

Michelle K. Lee
*Deputy Director of the United States Patent and Trademark Office*